Sept. 23, 1947. N. GRILLO Plant Pat. 762
ROSE PLANT
Filed June 12, 1946
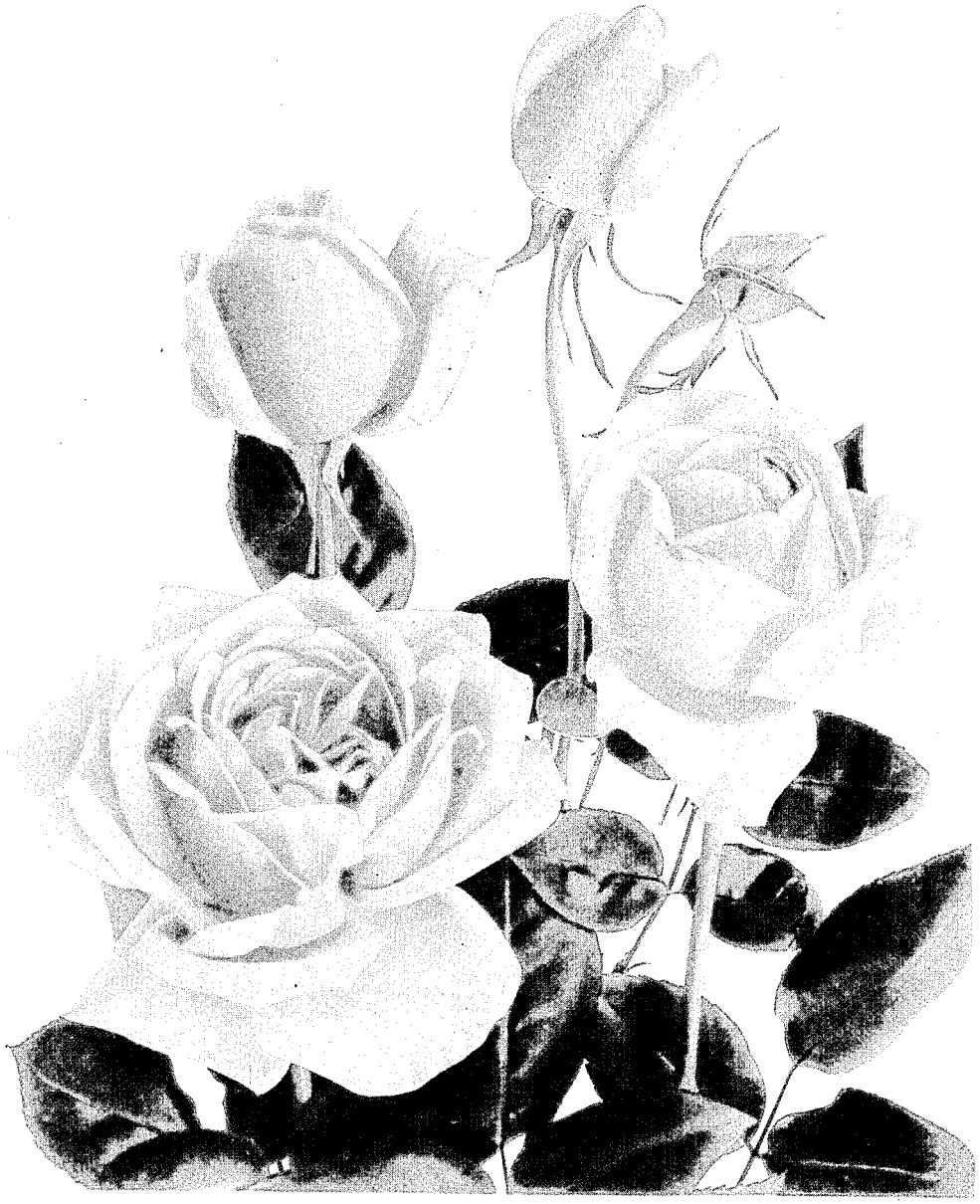
INVENTOR
Nicholas Grillo
By Orville M. Kile
Plant Pat. Agt.

Patented Sept. 23, 1947

Plant Pat. 762

UNITED STATES PATENT OFFICE

762

ROSE PLANT

Nicholas Grillo, Milldale, Conn.

Application June 12, 1946, Serial No. 676,426

1 Claim. (Cl. 47—61)

My present discovery relates to a new and distinct variety of hybrid tea rose. It was discovered by me in my greenhouses as a sport of the variety Jewel, the subject of Plant Patent No. 367. The growth and foliage characteristics are similar to those of its parent, but it is in an entirely different color class.

My new variety has been asexually reproduced for several years and its distinctive characteristics have proved to be firmly fixed.

The accompanying illustrations show several specimens of the flowers of my new variety in different stages of opening. In the original paintings these are shown in approximately their true size and colors.

In the following detailed description, color plate references are to Ridgway's Color Standards and Nomenclature.

*The plant*

Growth habits: Vigorous and free-growing, similar to that of its parent. Very hardy.

Form: Upright bush.

Blooming habit: Very free bloomer, producing an abundance of large, perfect flowers.

Foliage:

*Leaflets.*—Three to five.

*Size.*—Large; terminal leaflet measuring up to 3¼ inches long by 2 inches wide.

*Shape.*—Long oval with acute apex and rounded base. Edge shallowly serrate.

*Quantity.*—Abundant.

*Aspect.*—Glossy above, dull below.

*Color.*—Approximately Forest Green (Plate XVII).

*Stipules.*—Long, pointed and narrow.

*Rachis.*—Heavy; grooved above. Some prickles are found on under side.

Stems: Long, straight, and strong. Same color as peduncle.

Thorns: Stems smooth, almost devoid of thorns.

*The flower*

Bud:

*Size.*—Large; measuring approximately 2 inches long just before unfurling.

*Form.*—Pointed when small, becoming globular later.

Color.—Approximately Tyrian Rose (Plate XII).

*Opening.*—Opens slowly.

*Peduncle.*—Straight and strong; short to medium; approximately Rainette Green (Plate XXXI); almost free of spines or prickles.

*Sepals.*—Long; usually foliaceous. Do not reflex early.

Bloom:

*Borne.*—Singly.

*Form.*—Globular. One of the most outstanding features of this rose is the globular form which it retains throughout its life. Although the petals roll backward slightly at the edges they remain close together in a compact form. Just before shattering, the central petals usually spread open to reveal the yellow stamens and pistils.

*Size.*—Large; when fully expanded, measures up to 5 inches across.

*Color.*—The color would popularly be called Cerise or American Beauty. The nearest in Ridgway's lies between Tyrian Pink and Tyrian Rose (Plate XII).

*Petalage.*—Including very small petals, the petalage is 65 to 75 in May.

*Fragrance.*—Very intense.

*Lasting quality.*—Lasts a very long time.

*Behavior.*—Retains shape and the petals cling tenaciously.

Petals:

*Size.*—Outer petals measure about 2 inches in diameter in each direction.

*Form.*—Outer petals are round; inner petals narrower. All are deeply cupped, which feature aids materially in helping the flower to retain its form.

*Substance.*—Heavy.

Reproductive organs:

*Pistils.*—Many; tightly bunched; short. Styles white, tipped with yellow stigmas.

*Stamens.*—Few, surrounding bunched pistils. Filaments short and white. Anthers bright yellow.

Having thus disclosed my discovery, I claim:

The new and distinct variety of hybrid tea rose plant, substantially as herein shown and described, characterized particularly by its vigorous growth, its free blooming habits; its large flowers having distinctive form, intense fragrance, cerise color, and superior keeping qualities.

NICHOLAS GRILLO.